(12) United States Patent
Garavaglia et al.

(10) Patent No.: US 8,877,935 B2
(45) Date of Patent: Nov. 4, 2014

(54) ONE-POT PROCESS FOR THE SYNTHESIS OF DALFAMPRIDINE

(75) Inventors: Fabio Garavaglia, Cerano (IT); Alessandro Barozza, Nosate (IT); Jacopo Roletto, Turin (IT); Paolo Paissoni, Druento (IT)

(73) Assignee: Procos S.p.A., Cameri (IT)

( * ) Notice: Subject to any disclaimer, the term of this patent is extended or adjusted under 35 U.S.C. 154(b) by 200 days.

(21) Appl. No.: 13/154,866

(22) Filed: Jun. 7, 2011

(65) Prior Publication Data

US 2011/0319628 A1    Dec. 29, 2011

(30) Foreign Application Priority Data

Jun. 8, 2010   (IT) ................ MI2010A1015

(51) Int. Cl.
C07D 213/73    (2006.01)
A61K 31/44     (2006.01)
C07D 213/74    (2006.01)

(52) U.S. Cl.
CPC .................................... *C07D 213/74* (2013.01)
USPC ......................................... 546/311; 514/352

(58) Field of Classification Search
None
See application file for complete search history.

(56) References Cited

PUBLICATIONS

CASREACT Accession No. 141:277458 (2004).*
Poziomek J Org Chem 1963 vol. 28, pp. 590-591.*

* cited by examiner

*Primary Examiner* — Heidi Reese
(74) *Attorney, Agent, or Firm* — Arent Fox LLP

(57) ABSTRACT

A process for the preparation of Dalfampridine (1), 4-aminopyridine, starting from 4-pyridinecarbonitrile using a one-pot procedure.

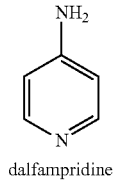

dalfampridine

Said process is carried out with no need for isolating intermediates and is particularly advantageous as far as environment, yields, productivity and purity of the resulting product are concerned, both in the reaction mixture and in the isolated crystal.

10 Claims, No Drawings

ONE-POT PROCESS FOR THE SYNTHESIS OF DALFAMPRIDINE

CROSS-REFERENCE TO RELATED APPLICATION

This application claims priority to Italian Application No. MI2010A001015 filed on Jun. 8, 2010. The disclosure of the prior application is hereby incorporated by reference herein in its entirety.

SUMMARY OF THE INVENTION

The present invention relates to a process for the preparation of Dalfampridine by reaction of 4-pyridinecarbonitrile with an oxidizing agent in the presence of a base.

TECHNICAL BACKGROUND

Dalfampridine (fampridine, 4-aminopyridine or 4-AP) is a medicament recently authorized in the USA for the improvement of deambulation in patients suffering from multiple sclerosis (SM). Dalfampridine acts blocking potassium channels and increasing the neurotransmitter release at the neuromuscular junctions.

4-Aminopyridine is known since 1902 and to date it has been synthesized following a number of synthetic routes.

The synthesis of Dalfampridine 1 is described starting from 4-nitro pyridine oxide 2 according to the following scheme:

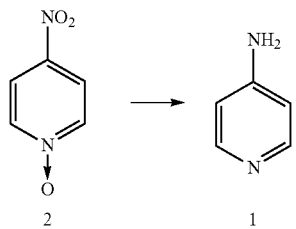 [SMILES: O=[N+]([O-])c1cc[n+]([O-])cc1 ; Nc1ccncc1]

Numerous articles describe this process as providing usually high yields. Recueil 1950. 69, 468 describes the reduction with iron and acetic acid; Journal fuer Praktische Chemie 1990. 332(3), 423-424 describes the use of a titanium tetrachloride and copper dichloride 1:2 mixture; while Chemical & Pharmaceutical Bulletin 1959, 2, 141-145 describes the use of hydrogen and Raney nickel. A number of other reduction methods have been described, for example lithium chloride and sodium borohydride in Synthetic Communications 2000. 30(19), 3511-3515; palladium on charcoal, acetic acid and sodium hydrophosphite monohydrate in Gazzetta Chimica Italiana 1994, 124(9), 385-386; titanium tetrachloride in PL149935; titanium in Journal fuer Praktische Chemie (Leipzig) 1988, 330(1); iron and acetic acid in Huaxue Shiji 54-8, 1998, 20(4), 240-241; hydrogen/nickel in Zhongguo Yiyao Gongye Zazhi 2001, 32(2), 83-84; hydrogen/Raney nickel in CN 1311185; zirconium tetrachloride/sodium borohydride in Chemistry Letters 1999, (12), 1339-1340; hydrogen/palladium in Jingxi Huagong 1999, 16(4), 39-43.

All the above mentioned procedures involve the use, in the last synthetic step, of either harmful heavy metals or very expensive precious metals, all of them, if present, being incompatible with a product for the pharmaceutical use. A number of known processes further involve the use of dangerous, self-flammable compounds. Furthermore, compound 2 has to be synthesized through direct nitration according to the scheme:

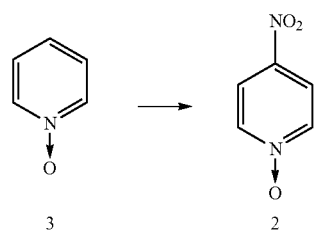 [SMILES: [O-][n+]1ccccc1 ; O=[N+]([O-])c1cc[n+]([O-])cc1]

Nitration is carried out with sulfuric acid and finning nitric acid (Recueil 1950. 69, 468). A similar procedure is disclosed in Huaxue Shiji (1998), 20(4), 240-241.

The process involves the use of very strong acids and of a nitration procedure which can lead to impure reaction mixtures difficult to separate from any regioisomeric secondary products (Organic Chemistry, Jonathan Clayden, Nick Greeves, Stuart Warren & Peter Wothers, 1153).

Moreover, compound 3 has to be prepared from pyridine 4 according to the following scheme:

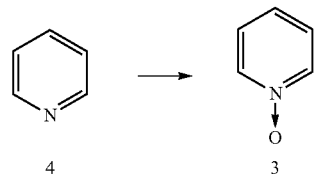 [SMILES: c1ccncc1 ; [O-][n+]1ccccc1]

Huaxue Shiji (1998), 20(4), 240-241 describes the reaction using hydrogen peroxide and acetic acid, namely potentially explosive peroxides.

The overall synthesis involves three steps, low overall yields and difficult isolation of two intermediates.

A synthesis of Dalfampridine is also described starting from isonicotinamide according to the following scheme:

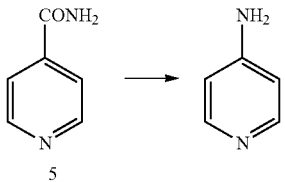 [SMILES: NC(=O)c1ccncc1 ; Nc1ccncc1]

The process, described in Journal of Chemical Technology and Biotechnology 1994, 59(3), 271-277, involves the Hofmann rearrangement using phase transfer catalysts. Similar processes are disclosed in CN 1807415 (rearrangement with molecular iodine and bromine), Xinan Minzu Daxue Xuebao, Ziran Kexueban 2004, 30(4), 425-428 and Yingyong Huaxue 2004, 21(5), 530-531 (molecular bromine).

The use of molecular bromine can lead to ring bromination by-products. The intermediate N-bromoamides are indeed known brominating agents, analogously to NBS in the Wohl-Ziegler reaction (J. Am. Chem. Soc. 1954, 76, 1388).

Furthermore, compound 5 has to be synthesized from 4-pyridinecarbonitrile starting material according to the following scheme:

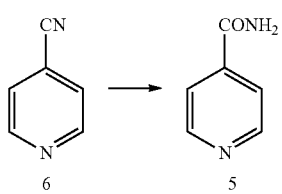 [SMILES: N#Cc1ccncc1 ; NC(=O)c1ccncc1]

The process is described in: Journal of the Chemical Society, Perkin Transactions 1: Organic and Bio-Organic Chemistry 1997, (8), 1099-1104 (enzymatic hydrolysis), US 2006 0155131 (manganese dioxide), Angewandte Chemie International Edition 2004, 43, 1576-1580 (alumina-supported ruthenium hydroxide), Tetrahedron Letters 2000. 41, 3747-3749 (potassium trimethylsilanolate), Tetrahedron Letters 2003, 44, 4031-4033 (sodium nitrate modified with fluoroapatite), Molecules [Electronic Publication] 2000. 5(2), 118-126 (NaY zeolite), Synthetic Communications 1993, 23, 3149-3155 (peroxides), Faming Zhuanli Shenqing Gongkai Shuomingshu 101602718 (sodium hydroxide under reflux), Chemical Communications (Cambridge, United Kingdom) 2009, (22), 3258-3260 (Ag on hydroxyapatite under pressure), Chemistry—A European Journal 2009, 15(35), 8695-8697 (gold, high temperature and microwaves with low yields), Chemistry—A European Journal 2009, 15(7), 1582-1586 (ruthenium hydroxide and microwaves), IN 194989 (manganese dioxide), IN 192739 (manganese dioxide), Yingyong Huaxue 2004, 21(5), 530-531 (magnesium oxide and ferric oxide), WO 2002055670 (enzymatic catalysis), JP 2001204485 (enzymatic catalysis), WO 9905306 (enzymatic catalysis), Synthetic Communications 1990. 20. 1445-1451 (peroxides), Energy & Fuels 1990, 4(5), 555-61 (thermal hydrolysis at 250° C.), Tetrahedron 1989 45(11), 3299-306 (peroxides) and Journal of Biotechnology 1988, 8(1), 87-95 (enzymatic hydrolysis).

The procedures for the synthesis of intermediate 5 are therefore numerous. However, those providing higher yields make use of either dangerous compounds such as peroxides, expensive technologies such as enzymatic catalysis or harmful compounds such as heavy metals. More particularly, in order to prepare Dalfampridine, all the above mentioned procedures require isolation of compound 5, which negatively affects yields and makes the process more cumbersome.

Compound 5 can also be obtained by reaction of compound 7 with a chlorinating reagent to give 8 and subsequent reaction of the latter with ammonia according to the following scheme:

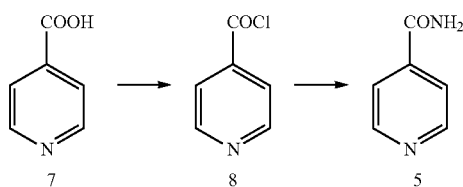 [SMILES: O=C(O)c1ccncc1 ; O=C(Cl)c1ccncc1 ; NC(=O)c1ccncc1]

The process is disclosed in Youji Huaxue 2006, 26(9), 1232-1238, Xinan Minzu Daxue Xuebao, Ziran Kexueban 2004, 30(4), 425-428, and Youji Huaxue 2003, 23(10), 1165-1168, Huaxue Xuebao 1986, 44(4), 417-20 describes the same process through a mixed anhydride. In both cases the technology is hardly efficient, both in terms of harmful chlorinating reagents used, and complexity of the synthesis as two further steps are required. In this case also, in view of producing Dalfampridine, intermediate 5 has to be isolated in a further step.

Chem. Commun., 2003, 1936-1937 describes the synthesis of 5 starting from aldoxime 11

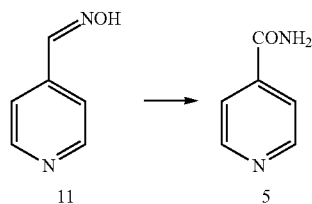

Compound 11 is obtainable using hydroxylamine, which is potentially explosive and hence poorly applicable on an industrial scale, and expensive starting materials. Furthermore, costly catalysts containing heavy metals are used.

Other synthetic methodologies for intermediate 5 are disclosed in Indian Journal of Chemistry, Section B: Organic Chemistry Including Medicinal Chemistry 2008, 47B(2), 315-318 and Chinese Chemical Letters 2007, 18(10), 1213-1217 which disclose the synthesis starting from 7 by use of a technology that cannot be applied industrially (microwaves on solid state).

The synthesis of Dalfampridine is further described in Heterocycles 1983, 20 (10), 1899-1901 starting from hydroxamic acid 10, which compound is not easily obtainable from methyl ester 9 and hydroxylamine.

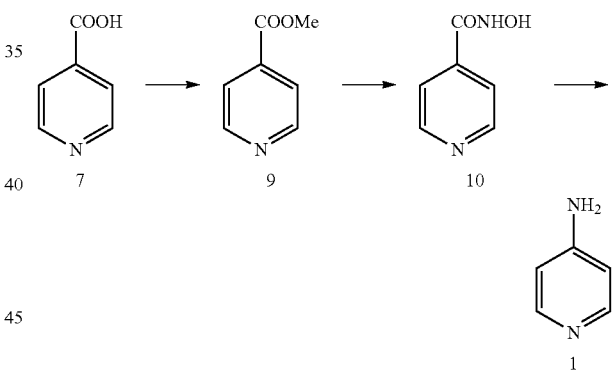

The synthesis involves three synthetic steps and he isolation of at least due intermediates.

The synthesis of Dalfampridine is also described in Chemical Communications (Cambridge, United Kingdom) 2009, 21, 3035-3037 starting from 4-halopyridine 12. Such halogenated compounds are industrially prepared from 1 and are remarkably more expensive than intermediates of type 5, 6 and 7.

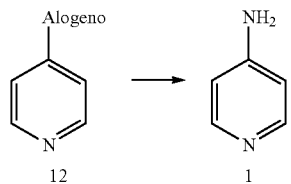

Furthermore, this process also makes use of catalysts containing heavy metals such as copper oxide.

The synthesis of Dalfampridine is further described in the Journal of the Chemical Society 1951, 1376 starting from intermediate 13 according to the following scheme:

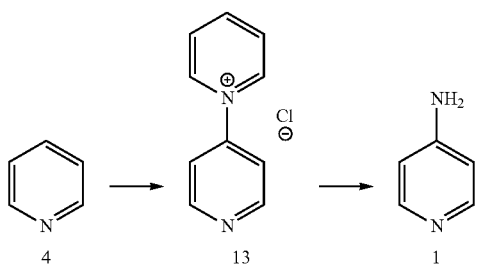 [SMILES: c1ccncc1 ; c1cc[n+](-c2ccncc2)cc1 ; [Cl-] ; Nc1ccncc1]

Compound 13 is not easy to prepare and the degradation reaction is carried out at 190° C. under ammonia gas flow.

US 2004/0106801 discloses a similar procedure with yields around 50%.

The preparation of Dalfampridine according to similar processes is also described in Recueil des Travaux Chimiques des Pays Bas et de the Belgique 1954, 73, 140-142, DE 566693, U.S. Pat. No. 4,140,853, DE 3241429.

The synthesis of Dalfampridine is also described in Recueil des Travaux Chimiques des Pays Bas et de the Belgique 1958, 77, 963-972 according to the following scheme:

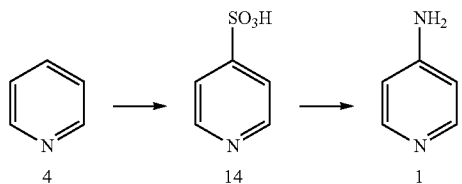 [SMILES: c1ccncc1 ; O=S(=O)(O)c1ccncc1 ; Nc1ccncc1]

The production of 14 involves a ring sulfonylation that can lead to impure reaction mixtures which are difficult to separate from any regioisomeric secondary products (Organic Chemistry, Jonathan Clayden, Nick Greeves, Stuart Warren & Peter Wothers, 1153). The yield is not very clear and the reaction of 14 to 1 is carried out at 180° C.

U.S. Pat. No. 4,672,121 discloses the preparation of Dalfampridine 1 according to the following scheme:

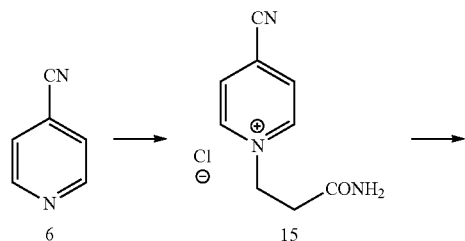

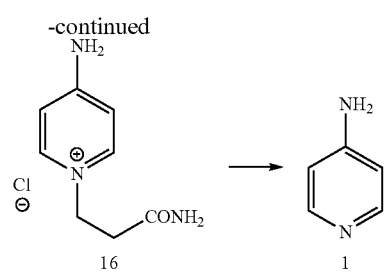

The process provides 40% yield from 15 to 1 and is not convenient.

Tetrahedron Letters 1975, (32), 2783-6 describes the synthesis of Dalfampridine according to the following scheme:

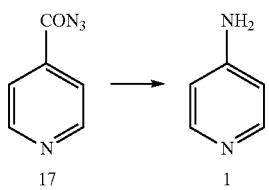

The synthesis comprises the formation of intermediate 17 through use of azides, which can be industrially used only with Tefloned installations, and it involves three synthetic steps starting from compound 7.

Finally, Gazzetta Chimica Italiana 1960. 90. 903-918 suggests the synthesis of Dalfampridine according to the following scheme:

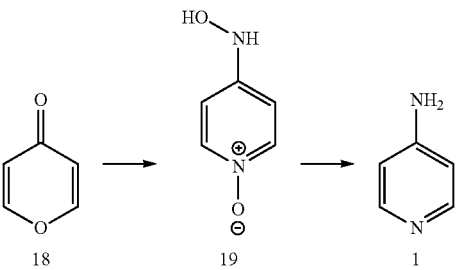 [SMILES: O=c1ccocc1 ; [O-][n+]1ccc(NO)cc1 ; Nc1ccncc1]

The starting material 18 is extremely expensive and overall process yields are low. Furthermore, hydroxylamine is used for the synthesis of 19.

DISCLOSURE OF THE INVENTION

An advantageous process has now been found for the preparation of Dalfampridine according to the following scheme:

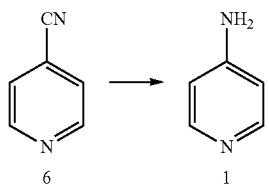 [SMILES: N#Cc1ccncc1 ; Nc1ccncc1]

The process of the invention comprises the reaction of intermediate 6, widely commercially available at very low prices, with an oxidizing agent in the presence of a base for preparing Dalfampridine 1 in a single step.

An inorganic base, for example NaOH, KOH and the like, is preferably used as the base.

Preferably, an agent capable of producing the halonium ion, preferably chloronium or bromonium, is used as the oxidizing reagent, e.g. molecular chlorine or bromine or hypochlorite or hypobromite salified with the cation of a strong base such as sodium or potassium.

In this case, the synthesis of Dalfampridine is carried out in a polar solvent, preferably a protic solvent such as water, in the presence of an inorganic base such as NaOH and an oxidizer such as sodium hypochlorite.

According to a preferred embodiment of the invention, the process is carried out as follows:

Typically, 4-pyridinecarbonitrile 6 is reacted with 1.0÷2.0 equivalents of the oxidizer, preferably sodium hypochlorite, preferably 1.0÷1.5 equivalents, in the presence of an inorganic base, preferably sodium hydroxide, in amounts ranging around 1.0÷2.5 equivalents, preferably 1.5÷2.0 equivalents. The reaction is carried out in a protic solvent, preferably water at a temperature of 20° C.÷100° C., preferably at a temperature of 40° C.÷80° C.÷25 volumes of solvent, preferably 10÷20 volumes, are used with respect to amount of the 4-pyridinecarbonitrile 6. The reaction is monitored by HPLC analysis using a Kinetex HILIC column and 0.1M buffer formate/acetonitrile as the phase eluent. After completion of the reaction, Dalfampridine 1 can be obtained by concentration of the solvent to small volume, cooling at 0° C.÷20° C., preferably at 0° C.÷10° C. and subsequent filtration of the resulting suspension. The filtered solid is dried under vacuum at a temperature of 30° C.÷90° C., preferably at a temperature of 30° C.÷60° C. The resulting solid is dissolved in 1÷4 volumes of an organic solvent, such as acetone, preferably 2÷3 volumes to the amount of dried solid. The suspension is heated at a temperature of 30° C.÷60° C., preferably at a temperature of 45° C.÷55° C. and filtered at this temperature. The filtered liquid mass is then concentrated to small volume, cooled to a temperature of 0° C.÷25° C., preferably at a temperature of 0° C.÷10° C. and filtered under vacuum at this temperature. The thus filtered solid is dried under vacuum at a temperature of 25° C.÷55° C., preferably at a temperature of 35° C.÷45° C., to obtain Dalfampridine 1.

The process of the invention is particularly advantageous in that is carried out very simply in a single step, without isolating any intermediate and from low cost starting materials. Furthermore, the process of the invention is also environmentally friendly as it follows the philosophy of the green chemistry, as it is completely performed in water, makes use of mild, harmless reagents and of only a class 3 solvent for the recrystallization of the final product.

The invention is illustrated in detail by the following examples.

EXPERIMENTAL SECTION

Example 1

Dalfampridine (1)

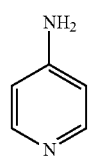

A solution of 4-pyridinecarbonitrile (6) (1 g, 0.0096 mol) in water (15 ml), is dropwise added at 35-40° C. under stirring with a solution of NaOCl (6.5 g, 0.0096 mol), then with NaOH (1.9 g, 0.014 mol). The mixture is then heated at 65-70° C. for 1 h, monitoring by HPLC. After completion of the reaction, the mixture is concentrated to a weight of 8 g, and left under stirring at 0-5° C. for 15', then filtered. The resulting solid is dried under vacuum at 50° C. for 16 h, then left under stirring in acetone (9 ml) at 50-55° C. for 15', finally filtered under vacuum. The clear solution is concentrated to a weight of 1.2 g, left under stirring at 0-5° C. for 30', then filtered under vacuum and dried under reduced pressure at 40-45° C. to obtain 0.74 g (81.9%) of a crystalline white solid.

Example 2

Dalfampridine (1)

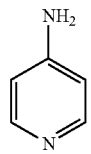

A solution of 4-pyridinecarbonitrile (6) (10 g, 0.096 mol) in water (140 ml), is dropwise added at 40-45° C. under stirring with a NaOCl solution (65 g, 0.096 mol) and with NaOH (23.1 g, 0.173 mol). The mixture is then heated at 65-70° C. for 1 h, monitoring by HPLC. After completion of the reaction, the mixture is concentrated to a weight of 70 g, then left under stirring at 0-5° C. for 30' and filtered. The resulting solid is dried under vacuum at 50° C. for 16 h, then left under stirring in acetone (80 ml) at 50-55° C. for 15', finally filtered under vacuum. The clear solution is concentrated to a weight of 12 g and left under stirring a 0-5° C. for 1 h, then filtered under vacuum and dried under reduced pressure a 40-45° C. to obtain 8.2 g (90.8%) of a crystalline white solid.

GC-MS (EI) m/z=94

$^1$H-NMR (in MeOH-$d_4$) (chemical shifts expressed in ppm with respect to the TMS signal): 4.96 (2H, s, $NH_2$); 6.48 (2H, d, J=4.9 Hz aromatic); 7.88 (2H, d, J=4.9 Hz, aromatic).

$^{13}$C-NMR (in MeOH-$d_4$) (ppm): 110.8 (2 CH aromatic); 150.2 (2 CH aromatic), 157.3 ($CNH_2$).

FT-IR (UATR, $cm^{-1}$): 3434, 3301, 3074, 1921, 1646, 1595, 1506, 1436, 1333, 1269, 1216, 989, 820.

m.p.: 158° C.

The invention claimed is:

1. A process for the preparation of Dalfampridine, comprising converting 4-pyridinecarbonitrile to Dalfampridine by reacting 4-pyridinecarbonitrile with an oxidizing agent in the presence of a base without isolating any intermediate:

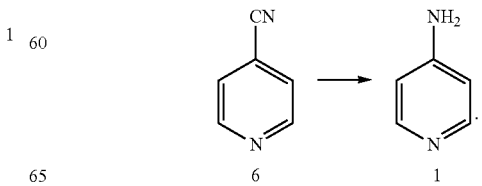

2. The process according to claim 1 wherein the base is an inorganic base.

3. The process according to claim 2 wherein the base is NaOH or KOH.

4. A process according to claim 1 wherein the oxidizing agent produces halonium ions.

5. The process according to claim 4, wherein the oxidizing agent is selected from molecular chlorine or bromine, or hypochlorite or hypobromite salified with the cation of a strong base.

6. A process according to claim 1 wherein the reaction is carried out in a polar solvent.

7. The process according to claim 6 wherein the solvent is water.

8. The process according to claim 1 wherein the reaction is carried out in water, the oxidizing agent is sodium hypochlorite and the base is NaOH.

9. A process according to claim 1, characterized in that the reaction is carried out in a single reaction vessel.

10. The process according to claim 5, wherein the cation of the strong base is selected from sodium or potassium.

* * * * *